US008383162B2

(12) United States Patent
Gómez et al.

(10) Patent No.: US 8,383,162 B2
(45) Date of Patent: Feb. 26, 2013

(54) PHα1B TOXIN, CDNA OF PHα1B TOXIN GENE, PHARMACEUTICAL COMPOSITION CONTAINING PHα1B TOXIN, PROCESS FOR THEIR PRODUCTION AND PRODUCT

(75) Inventors: Marcus Vinícius Gómez, Belo Horizonte (BR); Marco Antônio Máximo Prado, Belo Horizonte (BR); Vânia Ferreira Prado, Belo Horizonte (BR)

(73) Assignee: Universidade Federal de Minas Gerais, Belo Horizonte (BR)

( * ) Notice: Subject to any disclaimer, the term of this patent is extended or adjusted under 35 U.S.C. 154(b) by 9 days.

(21) Appl. No.: 12/515,619

(22) PCT Filed: Nov. 21, 2007

(86) PCT No.: PCT/BR2007/000318
§ 371 (c)(1),
(2), (4) Date: Feb. 22, 2010

(87) PCT Pub. No.: WO2008/061329
PCT Pub. Date: May 29, 2008

(65) Prior Publication Data
US 2010/0168009 A1 Jul. 1, 2010

(30) Foreign Application Priority Data
Nov. 21, 2006 (BR) .................................. 0605484

(51) Int. Cl.
*A61K 35/64* (2006.01)
*A61P 25/04* (2006.01)

(52) U.S. Cl. ...... 424/538; 514/18.3; 514/21.3; 530/324; 530/858

(58) Field of Classification Search .................. None
See application file for complete search history.

(56) References Cited

FOREIGN PATENT DOCUMENTS

| WO | 94/21278 | 9/1994 |
|----|----------|--------|
| WO | 2007/046634 | 4/2007 |

OTHER PUBLICATIONS

International Search Report for PCT/BR2007/000318, seven pages, mailed Jun. 18, 2008.

Written Opinion for PCT/BR2007/000318, ten pages, mailed Jun. 18, 2008.
Cardoso et al. "Molecular cloning and characterization of *Phoneutria nigriventer* toxins active on calcium channels" Toxicon, vol. 41, No. 7, pp. 755-763 (Jun. 1, 2003).
Cordeiro et al. "Purification and amino acid sequences of six TX3 type neurotoxins from the venom of the Brazilian 'armed' spider *Phoneutria nigriventer* (Keys.)" Toxicon, vol. 31, No. 1, pp. 35-42 (1993).
Layer & McIntosh "Conotoxins: Therapeutic potential and application" Marine Drugs, vol. 4, No. 3, pp. 119-142 (Apr. 2006).
Lewis & Garcia "Therapeutic potential of venom peptides" Nature Reviews Drug Discovery, vol. 2, No. 10, pp. 1474-1776 (Oct. 2003).
Liu et al. "Function and solution structure of huwentoxin-X, a specific blocker of N-type calcium channels, from the Chinese bird spider *Ornithoctonus huwena*" Journal of Biological Chemistry, vol. 281, No. 13, pp. 8628-8635 (Mar. 2006).
Pinheiro et al. "Neuroprotective effect on brain injury by neurotoxins from the spider *Phoneutria nigriventer*" Neurochemistry International, vol. 49, No. 5, pp. 543-547 (Oct. 2006).
Rajendra et al. "Toxins in anti-nociception and anti-inflammation" Toxicon, vol. 44, No. 1, pp. 1-17 (Jan. 1, 2004).
UNIPROT database "Neurotoxin PRTx23C2" Accession No. P84014 (Jun. 5, 2007).
Vieira et al. "PnTx3-6 a spider neurotoxin inhibits $K^+$ -evoked increase in $[Ca^{2+}]i$ and $Ca^{2+}$-dependent glutamate release in synaptosomes" Neurochemistry International, vol. 42, No. 4, pp. 277-282 (Mar. 2003).
Vieira et al. "Inhibition of high voltage-activated calcium channels by spider toxin PnTx3-6" Journal of Pharmacology and Experimental Therapeutics, vol. 314, No. 3, pp. 1370-1377 (Sep. 2005).

*Primary Examiner* — John Ulm
(74) *Attorney, Agent, or Firm* — Nixon & Vanderhye P.C.

(57) ABSTRACT

Methods and compositions for blocking calcium channels with a spider toxin from *Phoneutria nigriventer* are provided. For easy identification the toxin will be sometimes generally referred to as Phα-1B herein. The toxin comprises a 55-amino acid sequence having a molecular weight of approximately 6,017. This Phα-1B spider toxin was found to block calcium channels within the nervous system. The synthetic gene responsible for producing this toxin has been designed and cloned. This gene and/or its derivative provide a mechanism by which the toxin can be produced using recombinant DNA expression technologies. The present invention further relates to methods of treating neurological diseases and pain by applying the isolated and identified toxins. The toxin Phα-1B may provide beneficial effects on pain and certain neurological conditions including seizures, ischemic- hypoxic, CNS damage, and neurodegenerative disorders. It was also found that the toxins are effective as tags in probing calcium channels.

8 Claims, 3 Drawing Sheets

```
1         10             20            30            40            50
ACIPRGEICTDDCECCGCDNQCYCPPGSSLGIFKCSCAHANKYFCNRKKEKCKKA
```

```
 1   2   3   4   5   6   7   8   9  10  11  12  13  14  15  16  17  18  19  20
Ala Cys Ile Pro Arg Gly Glu Ile Cys Thr Asp Asp Cys Glu Cys Cys Gly Cys Asp Asn
```

```
21  22  23  24  25  26  27  28  29  30  31  32  33  34  35  36  37  38  39  40
Gln Cys Tyr Cys Pro Pro Gly Ser Ser Leu Gly Ile Phe Lys Cys Ser Cys Ala His Ala
```

```
41  42  43  44  45  46  47  48  49  50  51  52  53  54
Asn Lys Tyr Phe Cys Asn Arg Lys Lys Glu Lys Cys Lys Ala
```

Figure 1

SEQUENCE LISTING

```
<160> NUMBER OF SEQ ID NOS: 7

<210> SEQ ID NO 1
<211> LENGTH: 54
<212> TYPE: PRT
<213> ORGANISM: Phoneutria nigriventer
<220> FEATURE:
```

<221> NAME/KEY: Ph-alpha-1B toxin
<222> LOCATION: (1)...(54)

<400> SEQUENCE: 1

Ala Cys Ile Pro Arg Gly Glu Ile Cys Thr Asp Asp Cys Glu Cys Cys
                5                  10                  15
Gly Cys Asp Asn Gln Cys Tyr Cys Pro Pro Gly Ser Ser Leu Gly Ile
            20                  25                  30
Phe Lys Cys Ser Cys Ala His Ala Asn Lys Tyr Phe Cys Asn Arg Lys
        35                  40                  45
Lys Glu Lys Cys Lys Ala
    50

<210> SEQ ID NO 2
<211> LENGTH: 39
<212> TYPE: DNA
<213> ORGANISM: Escherichia coli (BL21 strain)
<220> FEATURE:
<221> NAME/KEY: PnTx36EcoF
<222> LOCATION: (1)...(39)

<400> SEQUENCE: 2
aattgaattc atcgagggaa gggcttgcat cccgcgtgg                            39

<210> SEQ ID NO 3
<211> LENGTH: 39
<212> TYPE: DNA
<213> ORGANISM: Escherichia coli (BL21 strain)
<220> FEATURE:
<221> NAME/KEY: PnTx36PSTR
<222> LOCATION: (1)...(39)

<400> SEQUENCE: 3
aattctgcag ttaagctttt ttacattttt cttttttac                            39

<210> SEQ ID NO 4
<211> LENGTH: 80
<212> TYPE: DNA
<213> ORGANISM: Escherichia coli (BL21 strain)
<220> FEATURE:
<221> NAME/KEY: Tx36F
<222> LOCATION: (1)...(80)

<400> SEQUENCE: 4
catcccgcgt ggtgaaattt gcaccgatga ctgtgaatgc tgcggctgtg acaaccaatg    60
ttattgcccg ccgggttcct                                                 80

<210> SEQ ID NO 5
<211> LENGTH: 80
<212> TYPE: DNA
<213> ORGANISM: Escherichia coli (BL21 strain)
<220> FEATURE:
<221> NAME/KEY: Tx36R
<222> LOCATION: (1)...(80)

<400> SEQUENCE: 5
tttctttttt acggttacaa aaatatttat ttgcatgtgc acacgagcat ttaaagatac    60
ccagcgagga acccggcggg                                                 80

<210> SEQ ID NO 6
<211> LENGTH: 168
<212> TYPE: DNA
<213> ORGANISM: Phoneutria nigriventer
<220> FEATURE:
<221> NAME/KEY: Ph-alpha-1B toxin

```
<222> LOCATION: (1) ... (168)

<400> SEQUENCE: 6
gcttgcatcc cgcgtggtga aatttgcacc gatgactgtg aatgctgcgg ctgtgacaac      60
caatgttatt gcccgccggg ttcctcgctg ggtatcttta aatgctcgtg tgcacatgca     120
aataaatatt tttgtaaccg taaaaaagaa aaatgtaaaa aagcttaa                 168

<210> SEQ ID NO 7
<211> LENGTH: 55
<212> TYPE: PRT
<213> ORGANISM: Phoneutria nigriventer
<220> FEATURE:
<221> NAME/KEY: Ph-alpha-1B toxin
<222> LOCATION: (1) ... (55)

<400> SEQUENCE: 7

Ala Cys Ile Pro Arg Gly Glu Ile Cys Thr Asp Asp Cys Glu Cys Cys
              5                  10                  15

Gly Cys Asp Asn Gln Cys Tyr Cys Pro Pro Gly Ser Ser Leu Gly Ile
             20                  25                  30

Phe Lys Cys Ser Cys Ala His Ala Asn Lys Tyr Phe Cys Asn Arg Lys
         35                  40                  45

Lys Glu Lys Cys Lys Lys Ala
     50                  55
```

PHα1B TOXIN, CDNA OF PHα1B TOXIN GENE, PHARMACEUTICAL COMPOSITION CONTAINING PHα1B TOXIN, PROCESS FOR THEIR PRODUCTION AND PRODUCT

This application is the U.S. national phase under 35 U.S.C. 371 of International Application No. PCT/BR2007/000318 filed 21 Nov. 2007, which designated the U.S. and claims priority to Application No. BR P10605484-6 filed 21 Nov. 2006; the entire contents of each of which are hereby incorporated by reference.

FIELD OF THE INVENTION

The present invention generally relates to the isolation of certain toxins from the venom of the spider *Phoneutria nigriventer* and the use of those toxins as inhibitors of the function of ionic channels. In particular, the present invention relates to the use of the spider *Phoneutria nigriventer* venom toxins and their isoforms as blockers of calcium channels in the central nervous and neuromuscular systems of organisms, including humans.

BACKGROUND OF THE INVENTION

Movement of calcium ions across cell membranes is a critically important event in the normal functioning of excitable tissues such as vascular smooth muscle, cardiac muscle, and the central nervous system. Influx of calcium ions through specialized channels in the cell membrane regulates the release of substances such as hormones and neurotransmitters.

Drugs that interfere with calcium influx in neurons are used in the treatment of the pain. In the treatment of hyperalgesia and alodinia it has been suggested that drugs that block calcium channels are more effective in the treatment of the pain than antagonists for individual receptors as NMDA, BK1, NK2 and CGRP. This advantage is due to the fact that calcium channel blockers do not develop tolerance as morphine does and they interfere with the release of neurotransmitters involved in nociception. With the exception of an omega-conotoxin ziconotide, disclosed in WO 9954350, and isolated from the snail Conus magnus no other drug with sufficient specificity or potent effect on the diverse forms of pain is known.

Patent document U.S. Pat. No. 6,489,298 relates to contulakin-G, analogs thereof and uses thereof in the native form or cDNA in formulations with application in pain processes associated with thrombosis, gastrointestinal disorders, analgesia, ulcers, tumors.

In WO02079236, an alpha-conotoxin peptide is used in the treatment or prevention of pain, in recovery from nerve injury, and in the treatment of painful neurological conditions. Alpha-conotoxin peptides are also described as being useful for muscle relaxation and neuromuscular blocking agents, in U.S. Pat. No. 6,268,473.

Technologies related to spider toxins are also found in the prior art. Document EP1161951 describes the toxin of spider *Selenoscomia huwena*, the peptide of which can be applied parenterally or topically in the treatment of pain and inhibition of calcium channel activity.

Patent document U.S. Pat. No. 5,281,693 discloses methods and compositions with the use of oligonucleotides obtained from the toxin of spider *Agelenopsis aperta*, for blocking $Ca^{2+}$ channels, and their use in the treatment of neurological disorders.

More common is the use of morphine and derivatives thereof with wide application in the treatment of nociceptive processes and analgesia procedures. However, its efficacy is for a short period of time, requiring new doses. In view of new technologies with a large spectrum of action and duration, the possibility of developing tolerance to the medication reduces its application.

As already mentioned above, the movement of calcium ions regulates contraction of heart muscle and vascular smooth muscle in the wall of the blood vessels. Abnormal influx of calcium ions has been reported to play a role in the pathogenesis of various cardiovascular disorders (e.g. anoxic/ischemic heart disease, cardiac arrhythmias) and drugs capable of blocking the movement of calcium through calcium channels have been used for treatment of pain, cardiac arrhythmias, coronary artery diseases, cardiopathy and stroke.

The current used drugs, however, have non-specific physiological effects and varying tissues specificities that can lead to undesirable side-effects in patients. Moreover there are several known subtypes of calcium channels with varying physiological actions and no drug that specifically bocks certain of these subtypes is known.

Phα1β was more effective to inhibit pain without causing severe side effects as those observed with ω-conotoxin zicononotide. This toxin-induced antinociception caused on the animals side effects such as serpentine tail movements, body shaking and allodynia that were not observed with analgesic doses of Phα1β.

Phα1β injected intrathecally has a potent and longer antinociceptive effect on the inflammatory phase of formalin test than ω-conotoxin ziconotide. Thus the analgesic effect of Phα1β lasted for a longer period of time than that observed for ω-conotoxin ziconotide.

The spinal dose-response curves showed that Phα1β displayed lower $ED_{50}$ values for inhibiting the inflammatory phase of formalin test, than that observed with ω-conotoxin ziconotide.

In the nervous system, calcium influx into the presynaptic nerve terminal via calcium channel is a necessary prerequisite for the release of chemical neurotransmitter at synapses and thus for the proper functioning of these synapses. Lowering the extracellular calcium is routinely used by neurophysiologist to reduce or abolish synaptic transmission in isolated pieces of nervous tissue.

ω-conotoxin ziconotide and Phα1β caused inhibition of the capsaicin-induced increase of $[Ca^{2+}]_i$, which plays an important role in neurotransmitter release, by blocking N-type calcium channels on neuronal pre-synaptic membrane.

Phα1β presented higher efficacy than ω-conotoxin ziconotide to inhibit capsaicin-induced release of glutamate from nerve ending spinal cord of rats.

Most important, the antinociceptive effects of Phα1β were observed using doses that were around 15 times lower than those associated with side-effects (DT50).

The recombinant form of Phα1β expressed in *E. coli* was capable to repeats the antinociceptive effects of the native toxin.

Phα1β may have a superior efficacy profile for relief of persistent pathological pain states than ω-conotoxin MVIIA.

Phα1β also showed higher efficacy than conotoxins against pain induced on the hot plate test. On this model of pain, Phα1β elevates thresholds, increasing significantly the latency period to 3, 4, 5, 6 and 24 hours after its administration In contrast, morphine only produced a significant effect that was initiated faster, but only lasted for up to 5 hours, a shorter time.

It has not been possible, however, specifically to affect synaptic transmission in vivo in the central nervous system (CNS) by manipulating the function of neuronal calcium channels. With the exception of the omega-conotoxin ziconotide isolated from the venom of the marine snail no drug with sufficient specificity or potent effects on CNS calcium channels is known. $Ph\alpha_{1B}$ may have the same properties of omega-conotoxin ziconotide without having the side effects observed for omega-conotoxin ziconotide.

Abnormal influx of calcium is thought to be very important in the pathogenesis of several CNS disorders, including anoxic/ischemic (stroke) damage, epilepsy, and the neuronal death associated with chronic epilepsy. Again, the paucity of chemical agents that potently and specifically block CNS calcium channels has impeded the development of an effective drug therapy for these prevalent neurological problems.

Thus, it would be a very considerable improvement in the art if it were possible to develop chemical agents that specifically and potently block calcium channel function in the CNS. In particular it would be advancement in the art to provide a specific blocker of particular subtypes of calcium channel. Similarly it would be advancement in the art to provide a specific blocker of calcium channels in the CNS.

Such chemical composition and methods for their use are disclosed and claimed below.

OBJECTS OF THE INVENTION

The present invention is related to the isolation, identification and use of spider Phoneutria Ph$\alpha_{1B}$ and other toxins contained within these venoms. In particular the present invention is related to the isolation and use as calcium channel blockers of certain toxins from spider venom.

As discussed above, calcium channels are intimately involved in pain and brain disorders. Calcium influx affects the diverse forms of pain, cerebral disorders and contraction of cardiac muscle and vascular smooth muscle. Similarly, calcium influx into nerve cells is required for the release of chemical neurotransmitter substances at synapses and, therefore, for the normal functioning of the nervous system. Calcium influx into nerve cells is also involved in mediating certain electrical responses of those cells. Abnormal calcium influx into cells is associated with disturbs of nociception, cardiovascular and brain ischemia.

The present invention is related to obtaining toxins from the spider *Phoneutria nigriventer* that have specific and potent blocking effects on calcium channels within the organism and thus are effective in the treatment of the pain, stroke and cardiovascular arrhythmias.

Within the scope of the present invention, spider venom of *Phoneutria nigriventer* is obtained by electrical stimulation. The electrical stimulation of the spider cause release of the venom and suction is used to collect the released venom. This assures that impurities, which have traditionally been contained within spider venoms obtained by conventional techniques are eliminated.

Spider venoms are known to be a complex mixture of enzymes, peptide toxins, nucleotides, free amino acids, and other molecules. As a result, in order to obtain useful spider toxins it is necessary to separate the various components of the whole spider venom. According to one embodiment of the present invention, whole venoms are fractionated by gel filtration on columns of Sephadex G-50 Superfine and Superose 12HR, and reverse phase FPLC on $C_2/C_{18}$ (PEP-RPC) and $C_1/C_8$ (PRO-RPC) columns. It will be appreciated, however, that any type of fractionation technique or other technique may be useful to obtain the toxins from the spider *Phoneutria nigriventer* necessary for use in the present invention.

A group of specific spider *Phoneutria nigriventer* toxins has been isolated and used extensively in the context of the present invention.

The aggressive South American "armed" or solitary wandering spider *P. nigriventer* occurs in north Argentina, Uruguay, Paraguay, Central- and South East Brazil. Specimens found in Montevideo, Uruguay, and Buenos Aires, Argentina have probably been introduced by shipments of fruit. The classification is Spider (animal group), Ctenidae (family) and Phoneutria (genus).

The primary specific toxin Ph$\alpha_{1B}$ which falls within the scope of the present investigation has been isolated from the venom of the spider *Phoneutria nigriventer*. In particular, a relative high molecular weight toxin that suppresses synaptic transmission in the vertebrate central nervous system by blocking calcium channels suppressing the pain.

Ph$\alpha_{1B}$ has been identified by amino acid sequencing techniques as a 55-amino acid peptide. The toxin has the sequence described on FIG. 1. The composition has molecular weight of 6017.

The coding sequence that produces the Ph$\alpha_{1B}$ toxin was cloned by PCR, the "polymerase chain reaction" technique described by Saiki et al. (See R. K. Saiki et al., "Primer-directed enzymatic amplification of DNA with a thermostable DNA polymerase", Science 239, 487 (January 1988).

In order to clone the coding sequence of the toxin four primers were prepared. Information about their sequence is presented in Table 1. Two overlapping oligonucleotides, $S_1$ and $AS_1$ contained most of the coding region and were used as template for the amplification. Amplification was obtained using primers S-Eco and AS-PsT. These primers are specific for the 5' and 3' regions of the coding region and contained recognition sites for the restriction enzymes Eco RI and PstI respectively, in order to facilitate the cloning step. Primer S-Eco also contained a sequence encoding for a recognition site for the protease Factor Xa to allow that the recombinant Ph$\alpha_{1B}$ protein be cleaved from any added N-terminal tag after purification without adding any vector-derived residues to the protein.

The coding region was amplified by PCR, the product purified, digested and cloned in an appropriate vector. Restriction fragment analysis and DNA sequencing were used to confirm that the cloned product contains the complete coding sequence of Ph$\alpha_{1B}$. The sequence of the fragment to be cloned and the analysis of the translated peptide are presented in Table 2. The cloned fragment encodes a peptide identical to the mature Ph$\alpha_{1B}$, present in the venom of the *Phoneutria nigriventer* spider. Cloning of the coding sequence responsible for the production of Ph$\alpha_{1B}$ facilitates the production of the toxin by using recombinant DNA techniques and may result in the ability to genetically engineer different organisms, such as bacteria, yeast or plants to produce the toxin.

TABLE 1

Primers used for PCR amplification (SEQ ID NOS: 2 to 5, respectively) of the coding sequence of the toxin Ph$\alpha_{1B}$

| Name | Sequence | Size |
|---|---|---|
| S-Eco | 5'-AAT TGA ATT CAT CGA GGG AAG GGC TTG CAT CCC GCG TGG-3' | 39 |
| AS-Pst | 5'-AAT TCT GCA GTT AAG CTT TTT TAC ATT TTT CTT TTT TAC | 39 |

TABLE 1-continued

Primers used for PCR amplification (SEQ ID NOS: 2 to 5, respectively) of the coding sequence of the toxin Phα₁ᵦ

| Name | Sequence | Size |
|------|----------|------|
| S1 | 5'-CAT CCC GCG TGG TGA AAT TTG CAC CGA TGA CTG TGA ATG CTG CGG CTG TGA CAA CCA ATG TTA TTG CCC GCC GGG TTC CT-3' | 80 |
| AS1 | 5' TTT CTT TTT TAC GGT TAC AAA AAT ATT TAT TTG CAT GTG CAC ACG AGC ATT TAA AGA TAC CCA GCG AGG AAC CCG GCG GG-3' | 80 |

TABLE 2

Nucleotide sequence (SEQ ID NO: 6) of the DNA fragment to be cloned and amino acid sequence (SEQ ID NO: 7) of toxin Phα₁ᵦ

GCT TGC ATC CCG CGT GGT GAA ATT TGC ACC GAT GAC
TGT GAA TGC TGC GGC

ALA CYS ILE PRO ARG GLY GLU ILE CYS THR ASP ASP
CYS GLU CYS CYS GLY

TGT GAC AAC CAA TGT TAT TGC CCG CCG GGT TCC TCG
CTG GGT ATC TTT AAA

CYS ASP ASN GLN CYS TYR CYS PRO PRO GLY SER SER
LEU GLY ILE PHE LYS

TGC TCG TGT GCA CAT GCA AAT AAA TAT TTT TGT AAC
CGT AAA AAA GAA

CYS SER CYS ALA HIS ALA ASN LYS TYE PHE CYS ASN
ARG LYS LYS GLU

AAA TGT AAA AAA GCT TAA

LYS CYS LYS LYS ALA*

Analysis of the translated peptide sequence indicated a protein having a molecular weight of approximately 6,017 Daltons with 12 cysteine residues.

Phα₁ᵦ is found to block transmission in central nervous system cells by blocking calcium currents. It is particularly noteworthy that Phα₁ᵦ is not acutely toxic to the cells tested and does not affect the electrical excitability of the neurons themselves. Thus Phα₁ᵦ effects are not produced by acute cytotoxic action. Simply stated, CNS transmission is blocked without damaging the cells involved. In experiments using rats, Phα₁ᵦ reduces the pain without any side effect contrary to that observed with morphine.

It is a primary object of the present invention to provide calcium channel blockers and methods for their use which have specific and identifiable therapeutic effect on an organism without any side effect.

Another object of the present invention is to provide calcium channel blockers which affect the central nervous system.

It is another object of the present invention to provide calcium channel blockers for use as research tools and for use in the clinical setting.

It is also an object of the present invention to identify the amino acid sequence of Phα₁ᵦ toxin responsible for blocking synaptic transmission in the central nervous system.

It is a similar object of the present invention to clone a synthetic gene responsible for production of the Phα₁ᵦ toxin that blocks synaptic transmission.

Other objects of the present invention will become apparent upon reading the following detailed description and appended claims.

DESCRIPTION OF THE DRAWINGS

FIG. 1 shows the peptide sequence (SEQ ID NO: 1 at the bottom and SEQ ID NO: 7 at the top) of the toxin isolated from *Phoneutria nigriventer*.

Figure 2:
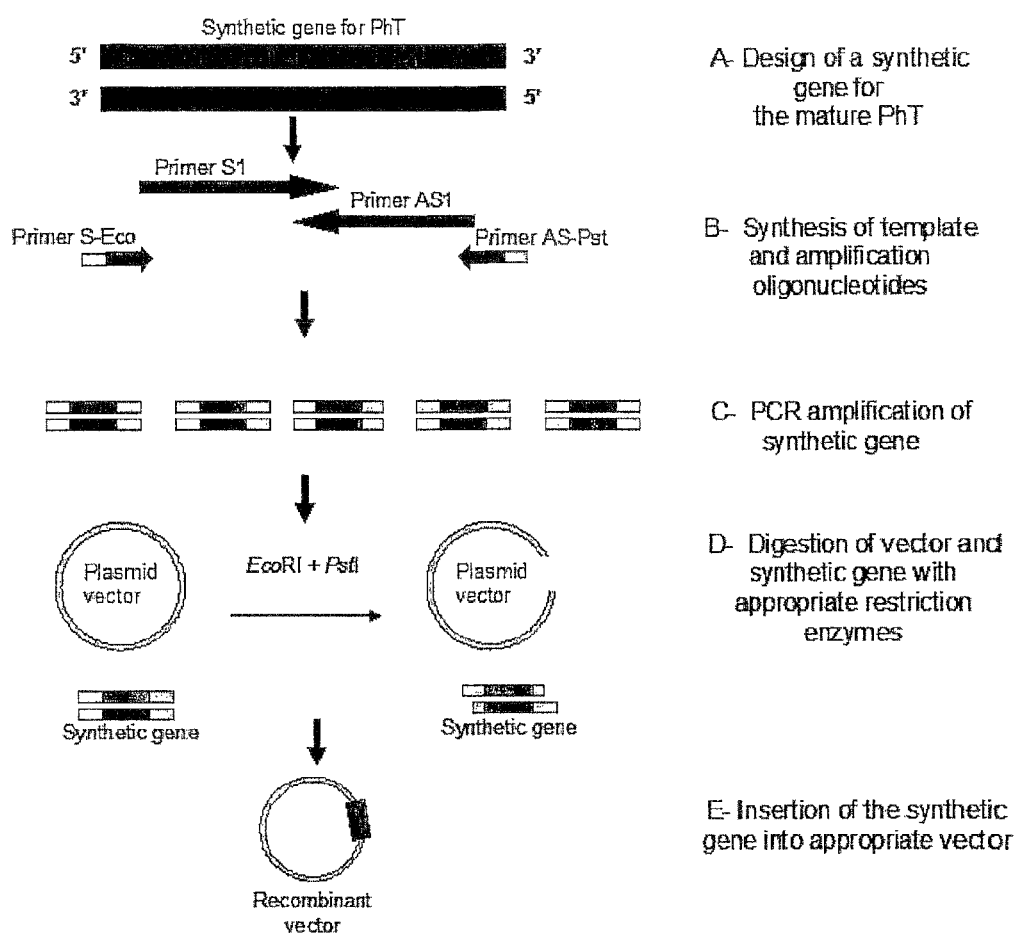
FIG. 2 refers to a schematic drawing representing the procedures employed in cloning a synthetic a gene responsible for production of Phα₁ᵦ.

Using the amino acid sequence data obtained as described above, a synthetic gene responsible for the production of the mature Phα₁ᵦ protein was designed (see nucleotide sequence in Table 2) and the procedures for its cloning were delineated. Both DNA strands of the gene are represented graphically in step (a), being the sense strand represented in red and the antisense strand in blue. The codons responsible for each amino acid in the synthetic gene were chosen using the *E. coli* codon preference, which is presented in Table 3. It is noteworthy that the possible number of sequences available to produce a 55-peptide is very large, due to the fact that some of the amino acids can be produced by up to six different codons.

TABLE 3

*E. coli* codon preference (adapted from Granthan et al., Nucleic Acids Research 9(1): 43-74 (1981))

| | | Bacteria | | | expression | |
|---|---|---|---|---|---|---|
| | | all | *E. coli* | other | high (13) | weak (16) |
| | | (29) | (25) | (4) | | |
| ARG | CGA | 4 | 3 | 8 | 0 | |
| | CGC | 21 | 21 | 20 | 17 | 24 |
| | CGG | 4 | 4 | 9 | 0 | 8 |
| | CGU | 30 | 30 | 26 | 44 | 18 |
| | AGA | 5 | 5 | 6 | 1 | 9 |
| | AGG | 2 | 2 | 1 | 0 | 4 |
| LEU | CUA | 3 | 2 | 7 | 0 | 5 |
| | CUC | 8 | 8 | 5 | 2 | 12 |
| | CUG | 47 | 47 | 47 | 58 | 39 |
| | CUU | 9 | 8 | 18 | 3 | 15 |
| | UUA | 9 | 7 | 21 | 3 | 14 |
| | UUG | 7 | 7 | 6 | 3 | 10 |
| SER | UCA | 8 | 8 | 9 | 1 | 13 |
| | UCC | 13 | 13 | 12 | 16 | 10 |
| | UCG | 9 | 9 | 5 | 3 | 14 |
| | UCU | 17 | 17 | 23 | 28 | 9 |
| | AGC | 9 | 9 | 13 | 10 | 9 |
| | AGU | 8 | 7 | 12 | 1 | 13 |
| THR | ACA | 5 | 5 | 6 | 4 | 6 |
| | ACC | 21 | 22 | 13 | 22 | 20 |
| | ACG | 9 | 10 | 7 | 1 | 16 |
| | ACU | 20 | 21 | 16 | 32 | 11 |
| PRO | CCA | 7 | 7 | 6 | 5 | 9 |
| | CCC | 5 | 4 | 8 | 1 | 8 |
| | CCG | 18 | 19 | 12 | 22 | 15 |
| | CCU | 5 | 5 | 7 | 5 | 6 |
| ALA | GCA | 31 | 31 | 28 | 43 | 21 |
| | GCC | 21 | 20 | 26 | 13 | 27 |
| | GCG | 24 | 23 | 28 | 21 | 26 |
| | GCU | 38 | 37 | 44 | 65 | 16 |
| GLY | GGA | 5 | 4 | 9 | 2 | 7 |
| | GGC | 29 | 29 | 32 | 32 | 27 |
| | GGG | 7 | 6 | 10 | 1 | 11 |
| | GGU | 30 | 33 | 14 | 45 | 19 |
| VAL | GUA | 20 | 21 | 16 | 32 | 11 |
| | GUC | 10 | 9 | 13 | 7 | 12 |
| | GUG | 17 | 17 | 14 | 14 | 19 |
| | GUU | 26 | 28 | 18 | 34 | 20 |
| LYS | AAA | 45 | 46 | 38 | 62 | 31 |
| | AAG | 17 | 18 | 12 | 19 | 15 |

TABLE 3-continued

E. coli codon preference (adapted from Granthan et al., Nucleic Acids Research 9(1): 43-74 (1981))

| | | Bacteria | | | expression | |
|---|---|---|---|---|---|---|
| | | all | E. coli | other | high | weak |
| | | (29) | (25) | (4) | (13) | (16) |
| ASN | AAC | 26 | 25 | 31 | 39 | 15 |
| | AAU | 11 | 10 | 19 | 3 | 18 |
| GLN | CAA | 14 | 13 | 19 | 8 | 18 |
| | CAG | 29 | 29 | 27 | 28 | 29 |
| HIS | CAC | 10 | 9 | 11 | 8 | 11 |
| | CAU | 15 | 16 | 14 | 10 | 20 |
| GLU | GAA | 36 | 37 | 29 | 39 | 33 |
| | GAG | 17 | 18 | 17 | 10 | 23 |
| ASP | GAC | 28 | 27 | 33 | 36 | 22 |
| | GAU | 25 | 25 | 30 | 16 | 33 |
| TYR | UAC | 13 | 12 | 14 | 14 | 12 |
| | UAU | 13 | 14 | 4 | 5 | 19 |
| CYS | UGC | 6 | 6 | 6 | 5 | 7 |
| | UGU | 5 | 5 | 4 | 1 | 8 |
| PHE | UUC | 17 | 18 | 11 | 15 | 19 |
| | UUU | 18 | 18 | 18 | 5 | 29 |
| ILE | AUA | 5 | 5 | 8 | 2 | 8 |
| | AUC | 31 | 32 | 25 | 42 | 22 |
| | AUU | 24 | 24 | 27 | 17 | 30 |
| MET | AUG | 22 | 22 | 20 | 19 | 25 |
| TRP | UGG | 11 | 12 | 5 | 5 | 16 |

Four oligonucleotides were designed in order to generate the synthetic gene and are represented as arrows in step (b). The oligonucleotide sequences are presented in Table 1. The sense oligonucleotide S1 contains the nucleotides encoding residues 3 through 28 of the mature $Ph\alpha_{1B}$. The antisense oligonucleotide AS1 overlaps with S1 and contains the nucleotides encoding residues 25 through 50. S1 and AS1 were used as template of the synthetic gene in the PCR reaction (see details in FIG. 2). Two other oligonucleotides were designed to be used as primers for the PCR reaction. The sense primer S-Eco contains the nucleotides encoding residues 1 through 6. The additional sequence AATTGAATTCATCGAGGGAAGG (SEQ ID NO: 2 from 1 to 22) was added at the 5' end of primer S-Eco. This sequence contains an EcoRI restriction site (underlined) followed by a sequence encoding a protease Factor Xa recognition site (double underlined). The antisense primer AS-Pst contains the nucleotides encoding residues 47 through 51 followed by an additional sequence that contains a stop codon and a PstI restriction enzyme site (CTGCAG).

These four oligonucleotides were used in a PCR reaction to produce the synthetic $Ph\alpha_{1B}$ gene (step c—see details in FIG. 2). PCR is well documented in the literature, including the citation set forth above. Essentially, PCR allows the production of a selected DNA sequence when the two terminal portions of the sequence are known. The synthetic gene was amplified over multiple cycles, as it is taught in PCR procedure. In this particular case amplification is going to take place over 40 cycles in order to assure maximum amplification.

The synthetic gene produced was digested with the appropriate restriction enzymes and cleaved at the engineered restriction site (step d). The digested gene sequence can then be cloned into an appropriate vector using conventional techniques, analyzed and sequenced. This step is illustrated at (e).

Figure 3:
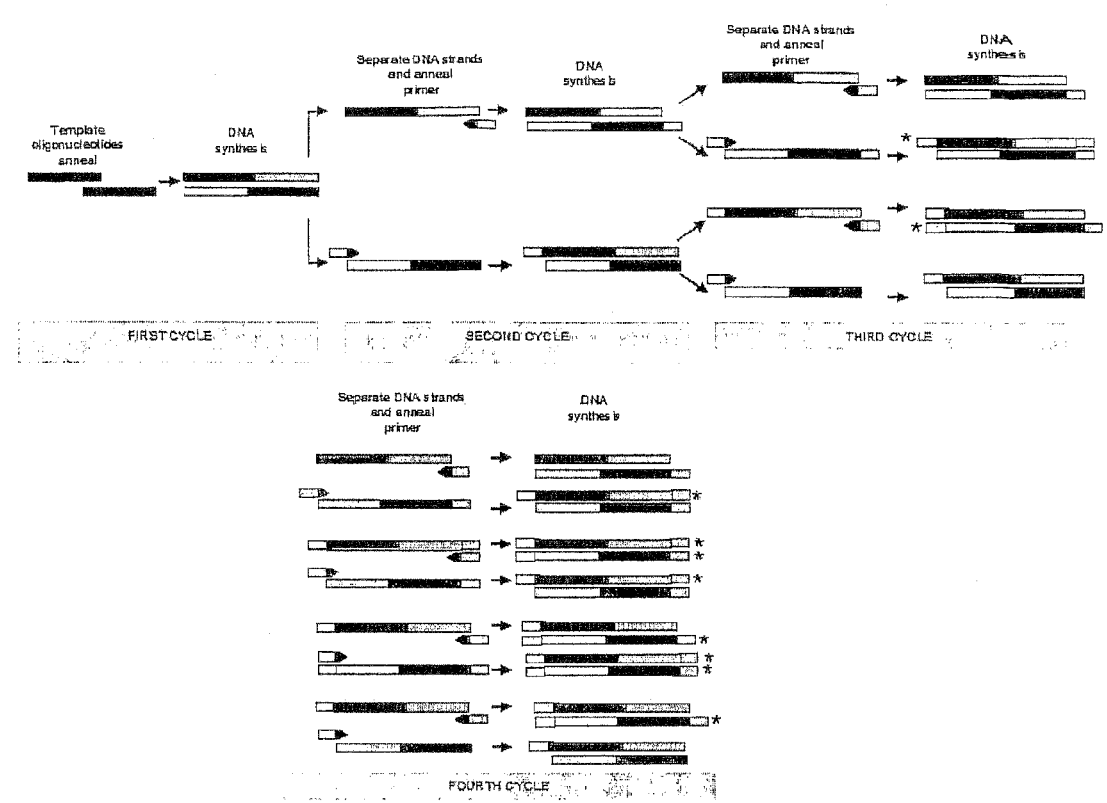

FIG. 3 shows a schematic drawing representing the initial steps during PCR amplification.

For this application, PCR amplification was prepared using two overlapping oligonucleotides as template (oligonucleotides S1 and AS1, shown in red and blue respectively; nucleotide sequences shown in Table 1) and two amplification primers (S-Eco and AS-Pst; shown as yellow-red and green-blue respectively; nucleotide sequences shown in Table 1). The four oligonucleotides were incubated with the appropriate amount of the four deoxynucleotides and the thermostable DNA polymerase and subjected to 40 cycles in a programmable heat block. Each cycle consists of denaturing the DNA at 94° C. for 2 minutes, annealing the primers for 1 minute at 55° C., and then extending the primers at 72° C. for 1 minute.

During the first cycle of the PCR amplification, the two overlapping template oligonucleotides anneal and the thermostable DNA polymerase extends these sequences generating a double stranded DNA that contains most of the synthetic $Ph\alpha_{1B}$ gene.

In the second cycle, the double stranded DNA generated in the first cycle was used as template. The strands are separated (94° C. for 2 minutes), the amplification primers anneal (55° for 1 minute) and the polymerase replicates the strands (72° C. for 1 minute). Note that in this cycle, the newly synthesized strand is longer than the template strand due to the additional sequences present at the 5' end of the amplification primers (indicated by yellow and green boxes).

The full-length Ph$\alpha_{1B}$ gene sequence flanked by restriction enzyme sites was first obtained in the third cycle. Complete strands are indicated by (*). From then on the number of complete sequences was increased exponentially as indicated in the fourth cycle.

DETAILED DESCRIPTION OF THE PREFERRED EMBODIMENTS

As discussed above, the present invention is related to new and unique calcium channel blockers, methods for their isolation, and methods of application of such molecules. In particular the present invention relates to the use of isolated toxins obtained from the venom of the spider Phoneutria nigriventer and their use as specific calcium channels blockers.

It has been found within the scope of the present invention that certain spider venoms may selectively act on the central nervous system. More particularly, it has been found that spider venoms can have specific activities on calcium channels with specific and identifiable therapeutic effect on the organism.

An additional benefit of the present invention is that the isolated toxins act without significant cytotoxicity and side effects. Thus the toxins block the channels without destroying the cells within the systems in which they are active. Additionally, the toxins of the present invention generally act without affection axonal conduction within the nervous system. It will be appreciated, therefore, that only calcium channels are affected by the toxin that acts on central nervous system.

I—Techniques for Isolation of Venom

To avoid impurities within the spider venom and the isolated toxins, the spider venom that was used for the tests, described below was electrically milked from the spiders using a method which employs safeguards to prevent contamination of the venom by abdominal regurgitate or hemolymph.

Once the spider venom is obtained it is further purified using gel filtration chromatography or other related technique. In addition, it is frequently desirable that the final fractionation of the spider venom be performed by high performance liquid chromatography (HPLC).

Thus, using the technique of electrically milking the spider coupled with gel filtration chromatography and high performance liquid chromatography it is possible to obtain purified and usable spider toxins. It will be appreciated, however, that other equivalent technique may also be employed and used.

II—Specific Toxin within the Scope of the Invention

While it will be appreciated that additional toxins may also fall within the scope of the present invention, the following relates to the identification and isolation of specific toxin which has been found to have the characteristics required for a usable calcium channel blocker as described above. In addition, a synthetic gene responsible for the production of the toxin is being cloned.

Using the techniques described above relating to the collection of the venom, a toxin has been isolated from *Phoneutria nigriventer* spider having a molecular weight of approximately 6017 and the following peptide sequence described on FIG. 1. It has been found that $Ph\alpha_{1B}$ blocks synaptic transmission, the influx of calcium on depolarized terminal and the release of excitatory neurotransmitter, glutamate.

Intrathecally administration of $Ph\alpha_{1B}$ in rats produced antinociception verified by formalin and hot plate tests. In these experiments the antinociceptive effect of $Ph\alpha_{1B}$ was higher than that induced by morphine. The $IC_{50}$ for the antinociceptive effect of $Ph\alpha_{1B}$ was 50.2 pmol and the maximal inhibition was obtained with a dose 87.2 pmol. The antinociceptive effect of $Ph\alpha_{1B}$ lasts up to 24 hours. Even at this concentration the toxin does not induce any side and adverse effects in the injected rats.

The toxin blocks the mammalian calcium channels expressed in HEK cells and whole-cell patch-clamp measurements shows that the $Ph\alpha_{1B}$ reversibly inhibited the N-type calcium channels with an $IC_{50}$ of 122 nM.

In summary the toxin exhibited measurable preference for N-type channels among the HVA $Ca^{2+}$ channels and the blockade of this channel is reversible. It has been shown that blockade of N-type calcium channels has pharmacological utility to treat pain and intratrathecal injection of low doses on of the toxin on the range of pmoles blocks pain transmission.

III—Comparison with Other Calcium Channel Blockers.

Receptor- and voltage-activated calcium channels are of fundamental importance in the survival and function of virtually all cell types. Entry of calcium through such channels regulates a variety of cellular activities including contraction of cardiovascular muscle and the release of neurotransmitters. There are presently three major known classes of organic calcium channel blockers, as opposed to inorganic blockers such as lanthanum or manganese. The organic calcium channel blockers include: phenylalkylamines such us verapamil, benzothiazepines such as diltiazem and dihydropyridine such as nifedipine.

The current available organic calcium channel blockers have pronounced action on heart and vascular smooth muscle, although relative selectivity for these two types of tissues varies among these compounds. A second notable feature of these agents is that, although they will bind to brain tissues, they have either no effect or a relatively minor effect on the function of neurons in CNS, particularly when compared to their striking effects on hearth and vascular smooth muscle.

The $Ph\alpha_{1B}$ toxin derived from *Phoneutria nigriventer* venom has properties that very clearly distinguish it from the currently available calcium channel blockers. $Ph\alpha_{1B}$ toxin acts primarily, if no exclusively, on neuronal calcium channels as opposed to heart or vascular smooth muscle calcium channels. This tissue selectivity is opposite to that seen in the compounds mentioned above.

In view of the importance of calcium and calcium channels to the function of neurons, there are a variety of potential applications of compounds within the scope of the present invention. Calcium influx through channels mediates neurotransmitter release and modulates neuronal excitability. Selective blockers of neuronal calcium channels, therefore, could modify neuronal excitability by effects on both presynaptic and postsynaptic calcium channels.

Accordingly, appropriate calcium channel blockers could be used in treatment of several neurological disorders that are thought to involve excessive neuronal excitation: e.g. stroke, traumatic head injury, epilepsy, and neurodegenerative disorders such as Huntington's disease and Alzheimer's disease.

Furthermore appropriate calcium channel blocker could be used in the treatment of the pain and on its diverse forms.

IV—Amino Acid Sequencing $Ph\alpha_{1B}$ was further analyzed in order to determine the amino acid sequence. The venom was obtained from *Phoneutria nigriventer* spiders using the techniques described herein. Active fractions of the venom were pooled and subject to separation on columns of Sephadex G 50 Superfine and Superose 12HR and reverse phase FPLC on $C_2/C_{18}$ (PEP-RPC) and $C_1/C_8$ (PRO-RPC) columns. The sequence of the toxin, FIG. 1, was performed using a model 477A automatic pulse liquid phase protein sequencer employing a standard Edman degradation sequenator program.

The results of the amino acid sequences analysis of $Ph\alpha_{1B}$ toxin yielded 55-amino acid peptide, FIG. 1. The peptide has a molecular weight in the range of 6017. The sequence of the peptide as identified by the procedure is:

Recombinant Expression

Provision of a suitable DNA sequence encoding the desired protein permits the production of the protein using recombinant techniques is well known in the art. The coding sequence can be obtained by retrieving a cDNA or genomic sequence from a native source of the protein or can be prepared synthetically using the accurate amino acid sequence from the nucleotide sequence of the gene. When the coding DNA is prepared synthetically, advantage can be taken of known codon preferences of the intended host.

Expression systems containing the requisite control sequences, such as, promoters, and preferably enhancers and termination controls, are readily available and known in the art for a variety of hosts.

Thus the desired proteins can be prepared in both prokaryotic and eukaryotic systems, resulting, in the case of many proteins, in a spectrum of processed forms. The most commonly used prokaryotic system remains *E. coli*, although other systems such as *B. subtillis* and *Pseudomonas* could also be used. Suitable control sequences for prokaryotic systems include both constitutive and inducible promoters including the lac promoter, the trp promoter, hybrid promoters such as tac promoter, and the lambda phage $P_1$ promoter. In general, foreign proteins may be produced in these hosts either as fusion or mature proteins. When the desired sequences are produced as mature proteins the sequence produced may be preceded by a methyonine which is not necessarily removed. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts is also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, oxidation or derivation of certain acid residues, conformational control, and so forth.

Commonly used eukaryotic systems include yeast, insect cells, mammalian cells, avian cells and cells of higher plants. Suitable promoters are available which are compatible and operable for use in each of these host types as well as are termination sequences and enhancers. As above, promoters can be either constitutive of inducible. For example, in mammalian systems, the MTII promoter can be induced by the addition of heavy metal ions.

The particulars for the construction of expression systems suitable for desired hosts are well known to those in the art. For recombinant production of the protein, the DNA encoding it is suitably ligated into the expression system of choice, and the system is then transformed into the compatible host which is then cultured and maintained under conditions wherein expression of the included gene takes place. The protein thus produced is recovered from the culture, either by lysing the cells or from the culture medium as appropriate.

A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein result from deletions, additions or substitutions. Such changes involving only 3 or less amino acid residues are generally preferred. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar. Furthermore, three of the encoded amino acids are aromatic. It is generally preferred that encoded peptides differing from the native form contain substituted codons for amino acids which are from the same group as that of the amino acid replaced.

The protein of the invention ($Ph\alpha_{1B}$) can be made recombinantly. Because of the variety of post-translational characteristics conferred by various host cells, various modifications for the naturally-occurring protein will also be obtained. A "modified" protein differs from the commonly occurring protein as a result of post-translational events which change the glycosylation or lapidation pattern, or the primary, secondary, or tertiary structure of the protein.

It should be further noted that if the protein herein ($Ph\alpha_{1B}$) is made synthetically, substitutions by amino acids which are not encoded by the gene may also be made. Alternative residues include, for example, phenylglycine, citrulline, methionine sulfoxide, cyclohexyl alanine, ornithine and hydroxyproline.

Example 1

A synthetic cDNA coding the mature $Ph\alpha_{1B}$ was cloned. The procedure can be outlined as follows:

1—Oligonucleotides containing the coding sequence for the mature $Ph\alpha_{1B}$ toxin were synthesized.

2—The oligonucleotides were used in PCR reactions to produce the complete coding sequence for the mature $Ph\alpha_{1B}$ flanked by restriction endonuclease sites.

3—The PCR amplified product was analyzed and isolated.

4—The PCR product was digested with appropriate enzymes, cloned and sequenced.

Step #1:

Two oligonucleotides were designed to be used as template for the PCR reaction. A sense oligonucleotide corresponding to residues 3 through 28 of the mature $Ph\alpha_{1B}$ (coding strand) and an overlapping antisense oligonucleotide corresponding to residues 25 through 50. Two other oligonucleotides were designed to be used as primers of the PCR reaction. The sense primer contained an Eco RI restriction enzyme site (GAATTC), followed by a sequence encoding a protease Xa recognition site (ATCGAGGGAAGG) (SEQ ID NO: 2 from 11 to 22) and nucleotides encoding residues 1 through 6. The antisense primer contained an PstI restriction enzyme site (CTGCAG) followed by an stop codon and nucleotides encoding residues 55 through 47. Primers were designed using the E. coli codon preference and were synthesized by IDT—Integrated DNA Technologies. Oligonucleotide sequence is presented in Table 1.

Step #2:

Primer directed enzymatic amplification of DNA with a thermostable DNA polymerase was initially described by Saiki et al. (Science, 239: 487 (1988)). For our application, the amplification reaction is going to contain the sense and antisense template oligonucleotides in a 0.1 µM concentration, the amplification primers in a 1 µM concentration, 250 µM of each deoxynucleotide triphosphate and 2 units of the thermostable recombinant Taq polymerase. The reaction was run in a programmable heat block manufactured by BioRad (USA). It was started by denaturing the DNA at 94° C. for 2 minutes, annealing the primers for 1 minute at 55° C., and then extending the primers at 72° C. for 1 minute. This cycle was repeated 40 times. After the final cycle, the samples were chilled at 4° C.

Step #3:

The PCR reaction was run on a 1.5% agarose gel in Tris/borate/EDTA (TBE) buffer in the presence of ethidium bromide. The gel was photographed and the band corresponding to the full length PCR (200 bp) was cut from the gel and purified using the QIAquick™ Gel Extraction kit (Qiagen, USA) to remove unincorporated primers.

Step #4:

The PCR product is then going to be digested with the restriction enzymes EcoRI and PstI (Invitrogen, USA), utilizing the restriction sites contained in the sense and antisense primers. The vector, pMAL-c2X (NewEngland BioLabs), is also going to be digested with EcoRI and PstI to generate sites specific for directional cloning. Vector and insert were ligated and transformed into competent E. coli strain DH5-α. Bacterial colonies were screened by PCR and candidate colonies were further characterized by sequencing mini-prep DNA using commercially available external primers.

Example 2

A spider toxin within the scope of the present invention was isolated from Phoneutria nigriventer spider. The identification of the specie provided in the Instituto de Ciencias Biológicas, UFMG, Belo Horizonte, MG, Brazil. Phoneutria nigriventer spiders were electrically milked using a method that employs safeguards to prevent contamination of the venom by abdominal regurgitate or hemolymph. The venom was fractionated by gel filtration chromatography on columns of Sephadex G-50 Superfine and Superose 12HR and reverse phase HPLC using Vydak C-18. The fractions were tested for the inhibition of glutamate release and calcium uptake in the synaptosomes. The column was eluted with a gradient of 0 to 40% (v/v) acetonitrile in 0.1% TFA over 180 min at a flow rate of 10 ml/min. Elutions was monitored by absorbance detection at 216 nm. Peaks were collected manually, dried down, stored at −20° C. in siliconized Eppendorf tubes and then reconstituted with saline solution. For gel electrophoresis SDS-PAGE was carried out using 22% gels. Gels were stained with Coomasssie Blue. High resolution propionic acid/urea was performed as described in the literature. Examination of the toxin by SDS-PAGE revealed their apparent molecular weight but more accurate estimates were obtained by subjecting the proteins to the Biolon time of flight plasma desorption mass spectroscopy method which yielded value of 6017,9. The toxin was bath-applied to stimulated synaptomes preparation. It was found that the toxin blocked the stimulated release of glutamate and the uptake of $^{45}Ca^{2+}$ in synaptosomes and by intratechal injection reduces the pain in rats without any side effect contrary to the observed with morphine.

Example 3

Male and female specimens of the spider were collected in the regions of Santa Barbara and Mariana, respectively, both in the State of Minas Gerais, Brazil. Venom from live adult spiders was obtained by electrical stimulation of the fangs. The venom was immediately transferred to siliconized glass tubes in ice, diluted with the same volume of distilled water and centrifuged at 4000 g to remove insoluble materials and debris. The supernatant was lyophilized and stored at −18° C. Aliquots of 25-30 mg of lyophilized venom were dissolved in 2 ml of aqueous 0.1 trifluoroacetic acid (TFA) and centrifuged at 4000 g for 10 min to remove insoluble materials. The brownish yellow supernatant was applied to preparative column (2.2×25 cm) of Vidac C4 equilibrated with 0.1 TFA in water (solvent A). Solvent B was 100% acetonitrile containing 0.1 TFA. The column was eluted with a flow rate of 5 ml/min with the following gradient system: 0 to 20 min, 100% A; 20 to 30 min, 0-20% B, 30-110 min, 20-40% B; 110-130 min, 40-50% B; 130-150 min 50-70% B. The presence of peptides or proteins in the eluate was detected by measuring the UV absorption at 214 nm. Fractions containing peptides were collected manually and lyophilized. The lyophilized fractions from the preparative reverse phase HPLC(RP-HPLC) were then dissolved in 2 ml of 10 mM sodium phosphate buffer pH 6.1 and subjected to ion-exchange FPL on a column (6.4 mm×30 mm) of Resource™ S equilibrated in the same buffer. A small number of fractions from the preparative RP-HPLC step which were not well resolved by using cation exchange chromatography were fractionated on anion exchange HPLC column of Synchropak AX-300 using linear gradient of 0-0.5 M NaCl in 10 mM Tris-HCl buffer pH 8.6 at a flow rate of 1 ml/min. The venom components obtained from these cation and anion exchange FPLC and HPLC steps were desalted and further purified by RP-FPLC or RP-HPLC on analytical columns of PepRPC™, Vydac C8 or C18 using gradients of acetonitrile in 0.1 TFA. The purity of all fractions obtained was examined by PAGE and mass spectroscopy on ES-Q-TOF spectrometer equipped with an electrospray ionization source. The amino acid sequences of the S-pyridyl-ethylated intact. The results of amino acid and sequence analyses of $Ph\alpha_{1B}$ are described on FIG. 1.

Example 4

The $Ph\alpha_{1B}$ toxin purified by the described procedure was tested on whole-cell patch clamp recordings performed on HEK cells transfected with cDNA coding for one type of calcium channels. The toxin produced a reversible block of all four HVA calcium channels subtypes (L, N, P/Q and R) but the inhibition was most potent and effective on N-type (al b) calcium channel.

Pretreatment with $Ph\alpha_{1B}$ by intratechal bolus injection showed that the toxin blocks the acute, cronic and neurogenic pain. In the heat pain model the antinociceptive effect of the $Ph\alpha_{1B}$ lasts 24 h.

The toxin so obtained was tested for its ability to block neurotransmitter release on in vitro synaptosome preparations from brain cortical slices. The toxin blocked the release of glutamate induced by K+ depolarization It will be appreciated that the present invention provides the ability to effectively block specific channels using the toxin. Similarly, specific channel blocker with activity on the central nervous system may have the potential to treat various neurological disorders. It has been found, for example that these channel blockers may act as a treatment of pain. In addition, channel blockers of the type disclosed in the present invention may also be used in treatment of stroke, traumatic head injury and degenerative central nervous system diseases such as Huntington disease and cardiac arrhythmias.

In summary, it can be seen that the method and compositions of the above invention accomplish the objectives set forth above. In particular, the present invention provides calcium channel blockers which can be used as research tools or in a clinical setting. In particular, the spiders of the present invention can be used as calcium channel blockers in the central nervous system.

According to the present invention the toxin may be embodied in other specific forms without departing from its spirit or essential characteristics. The described embodiments are to be considered in all respects only as illustrative and not restrictive. The scope of the inventions is therefore, indicated by the appended claims rather than by the foregoing description. All changes which come within the meaning and range of equivalency of the claims are to be embraced within their scope.

The invention claimed is:

1. A substantially pure peptide functioning as a calcium channel blocker for an N-type calcium channel and comprising the amino acid sequence of SEQ ID NO: 1 or an acceptable salt thereof.

2. A substantially pure peptide according to claim 1 which is produced in a genetically engineered organism selected from the group consisting of bacteria, yeast, and plants.

3. A substantially pure peptide according to claim 1 which is isolated from *Phoneutria nigriventer* venom.

4. A pharmaceutical composition containing a peptide of claim 1, and a pharmaceutically-acceptable carrier.

5. An isolated peptide toxin responsible for producing blockade of synaptic transmission in a vertebrate central nervous system comprising the amino acid sequence of SEQ ID NO: 1.

6. A peptide toxin according to claim 5 which is produced in a genetically engineered organism selected from the group consisting of bacteria, yeast, and plants.

7. A peptide toxin according to claim 5 which is isolated from *Phoneutria nigriventer* venom.

8. A pharmaceutical composition containing a peptide of claim 5 or an acceptable salt thereof, and a pharmaceutically-acceptable carrier.

* * * * *

UNITED STATES PATENT AND TRADEMARK OFFICE
CERTIFICATE OF CORRECTION

PATENT NO.      : 8,383,162 B2  
APPLICATION NO. : 12/515619  
DATED           : February 26, 2013  
INVENTOR(S)     : Gómez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this  
First Day of September, 2015

Michelle K. Lee  
*Director of the United States Patent and Trademark Office*